United States Patent
Seyama et al.

(10) Patent No.: US 7,262,410 B2
(45) Date of Patent: Aug. 28, 2007

(54) SAMPLE OBSERVING APPARATUS AND SAMPLE OBSERVING METHOD

(75) Inventors: Masahiro Seyama, Tokyo (JP); Masayuki Kuribara, Tokyo (JP); Toshihiko Hara, Tokyo (JP); Kazuhiro Arakawa, Tokyo (JP); Toshimichi Iwai, Tokyo (JP)

(73) Assignee: Advantest Corporation, Tokyo (JP)

( * ) Notice: Subject to any disclaimer, the term of this patent is extended or adjusted under 35 U.S.C. 154(b) by 149 days.

(21) Appl. No.: 11/165,572

(22) Filed: Jun. 23, 2005

(65) Prior Publication Data

US 2006/0006330 A1 Jan. 12, 2006

Related U.S. Application Data

(63) Continuation of application No. PCT/JP03/15476, filed on Dec. 3, 2003.

(30) Foreign Application Priority Data

Dec. 27, 2002 (JP) .............................. 2002-380192

(51) Int. Cl.
*G01N 23/00* (2006.01)
(52) U.S. Cl. ...................... 250/310; 250/307; 250/311
(58) Field of Classification Search ................. 250/310
See application file for complete search history.

(56) References Cited

U.S. PATENT DOCUMENTS

2002/0005484 A1* 1/2002 Nishimura ................. 250/310

2003/0213893 A1* 11/2003 Nagahama et al. ......... 250/210

FOREIGN PATENT DOCUMENTS

JP 2001-110347 4/2001
JP 2002-245960 8/2002

OTHER PUBLICATIONS

Patent Abstracts of Japan, Publication No. 2002-245960, Publication Date: Aug. 30, 2002, 2 pages.
Patent Abstracts of Japan, Publication No. 2001-110347, Publication Date: Apr. 20, 2001, 1 page.
International Search Report for PCT/JP03/15476 mailed on Mar. 16, 2004, 1 page.

* cited by examiner

*Primary Examiner*—Nikita Wells
*Assistant Examiner*—James J Leybourne
(74) *Attorney, Agent, or Firm*—Osha Liang LLP

(57) ABSTRACT

There is provided a sample observing apparatus for observing the surface of a sample by irradiating an electron beam thereto, having an electron gun for irradiating the electron beam to the surface of the sample, a potential control section for adjusting electric potential of the surface of the sample to potential set in advance by applying voltage determined based on an amount of electric charge on the surface of the sample to the sample, an electron detecting section for detecting electrons produced when the electron beam is irradiated to the surface of the sample and an appearance acquiring section for acquiring the appearance of surface of the sample per each spot on the surface based on the electrons detected by the electron detecting section.

9 Claims, 4 Drawing Sheets

SAMPLE OBSERVING APPARATUS AND SAMPLE OBSERVING METHOD

The present application is a continuation application of PCT/JP2003/015476 filed on Dec. 3, 2003, claiming priority from a Japanese Patent application No. 2002-380192 filed on Dec. 27, 2002, the contents of which are incorporated herein by reference.

BACKGROUND OF THE INVENTION

1. Field of the Invention

The present invention relates to a sample observing apparatus and a sample observing method for observing an appearance of surface of a sample and more specifically to an apparatus and a method for observing the appearance of surface of the sample by irradiating an electron beam thereto.

2. Description of Related Art

Conventionally, there is a scanning electron microscope for example as an apparatus for observing an appearance of surface of a sample. The conventional scanning electron microscope enables one to observe the appearance of surface of the sample by detecting secondary electrons produced when a beam of electrons is irradiated to the surface of the sample. At this time, acceleration voltage is applied to the electron beam produced by an electron gun in order to irradiate the beam to the surface of the sample. For instance, the electron beam is irradiated to the surface of the sample by setting electric potential of the surface of the sample at reference potential such as earth potential and by applying negative voltage to the electron gun. An apparatus for detecting the secondary electrons is disposed at position apart form the surface of the sample by an adequate distance.

The apparatus having the configuration as described above may acquire a secondary electron image showing the appearance of surface of the sample by scanning the surface of the sample by the electron beam. By the way, the electron beam needs to be focused on the surface of the sample in order to observe the surface of the sample with precision. To that end, the scanning electron microscope is provided with lenses for converging the electron beam.

However, the conventional apparatus has been unable to acquire the appearance of surface of the sample with precision when the surface of the sample is charged with electricity, thus causing potential different from the reference potential. When the surface of the sample is charged with positive electric charge for example, the produced secondary electrons may be attracted to the surface of the sample and may not be able to reach to the apparatus for detecting the secondary electrons. Therefore, it is unable to detect the secondary electrons with precision and is difficult to acquire the secondary electron image with precision accordingly.

Still more, when the surface of the sample is charged with electricity, the acceleration voltage of the electron beam may vary, thus varying the level of focus of the electron beam on the surface of the sample. Because the divergence of the electron beam on the surface of the sample depends on the level of focus of the electron beam, it is difficult to acquire the secondary electron image with precision also in this case.

It is therefore an object of the invention to provide a sample observing apparatus and a sample observing method that can solve the above-mentioned problems. This object may be achieved by combining features described in independent claims of the invention. Dependent claims specify further preferable embodiments of the invention.

SUMMARY OF INVENTION

In order to solve the above-mentioned problems, according to a first aspect of the invention, there is provided a sample observing apparatus for observing the surface of a sample by irradiating an electron beam, having an electron gun for irradiating the electron beam to the surface of the sample, a potential control section for adjusting electric potential of the surface of the sample to potential set in advance by applying voltage to the sample on the basis of an amount of electric charge on the surface of the sample, an electron detecting section for detecting electrons produced when the electron beam is irradiated to the surface of the sample and an appearance acquiring section for acquiring an appearance of surface of the sample per each spot on the surface based on the electrons detected by the electron detecting section.

Preferably, the sample observing apparatus is provided further with a sample holder for mounting the sample and the potential controlling section applies the voltage corresponding to the amount of electric charge of the surface of the sample to the sample by applying it to the sample holder to adjust the potential of the surface of the sample to the potential set in advance.

Preferably, the sample observing apparatus is also provided with a stage for mounting the sample holder and a stage control section for driving the stage to control the spot on the surface of the sample to which the electron beam is irradiated. Then, the potential control section may control the voltage to be applied to the sample holder per each spot on the surface of the sample to which the electron beam is irradiated corresponding to the amount of electric charge per each spot on the surface of the sample to adjust the electric potential at each spot on the surface of the sample to the potential set in advance.

Preferably, the potential control section has a memory for storing the spot on the surface of the sample correlatively with the voltage applied to the sample holder.

The sample observing apparatus may be provided further with an energy filter for sequentially sorting reflected electrons having energy higher than a predetermined value and secondary electrons having energy less than that of the reflected electrons among electrons produced when the electron beam is irradiated to the surface of the sample and supplying them to the electron detecting section; and a focusing judging section for judging levels of focus of the electron beam that vary corresponding to the amount of electric charge on the surface of the sample based on the reflected electrons detected by the electron detecting section. Then, the potential control section may control the voltage to be applied to the sample holder based on the judged result of the focusing judging section to focus the electron beam on the surface of the sample.

Preferably, the energy filter supplies the secondary electrons to the electron detecting section in a state when the electron beam is focused on the surface of the sample by the potential control section; and the appearance acquiring section acquires the appearance of surface of the sample based on the secondary electrons detected by the electron detecting section.

The focusing judging section may judge the level of focus based on the appearance of surface of the sample acquired by the appearance acquiring section based the reflected electrons.

Still more, the appearance acquiring section may acquire an image of the shape of surface of the sample based on the electrons detected by the electron detecting section; and the focusing judging section may judge the level of focus based on the variation of the brightness among pixels of the image acquired by the appearance acquiring section based on the reflected electrons.

According to a second aspect of the invention, there is provided a sample observing method for observing the surface of a sample by irradiating an electron beam, having a first irradiating step of irradiating the electron beam to the surface of the sample; a potential control step of adjusting electric potential of the surface of the sample to potential set in advance by applying voltage determined based on the amount of electric charge on the surface of the sample to the sample; an electron detecting step of detecting electrons produced when the electron beam is irradiated to the surface of the sample; and an appearance acquiring step of acquiring an appearance of surface of the sample based on the electrons detected in the electron-detecting step.

It is noted that the summary of the invention does not necessarily describe all necessary features of the invention. The invention may also be a sub-combination of the features described above.

BRIEF DESCRIPTION OF THE DRAWINGS

FIGS. 4A and 4B are graphs for explaining one example of a method for judging levels of focus of a focusing judging section, wherein FIG. 4A shows brightness of pixels of a reflected electron image acquired by an appearance acquiring section when an electron beam is not focused on the surface of a sample and FIG. 4B shows brightness of pixels of a reflected electron image acquired by the appearance acquiring section when the electron beam is focused on the surface of the sample.

DETAILED DESCRIPTION OF THE INVENTION

The invention will now be described based on preferred embodiments, which do not intend to limit the scope of the invention, but exemplify the invention. All of the features and the combinations thereof described in the embodiments are not necessarily essential to the invention.

Figure 1:
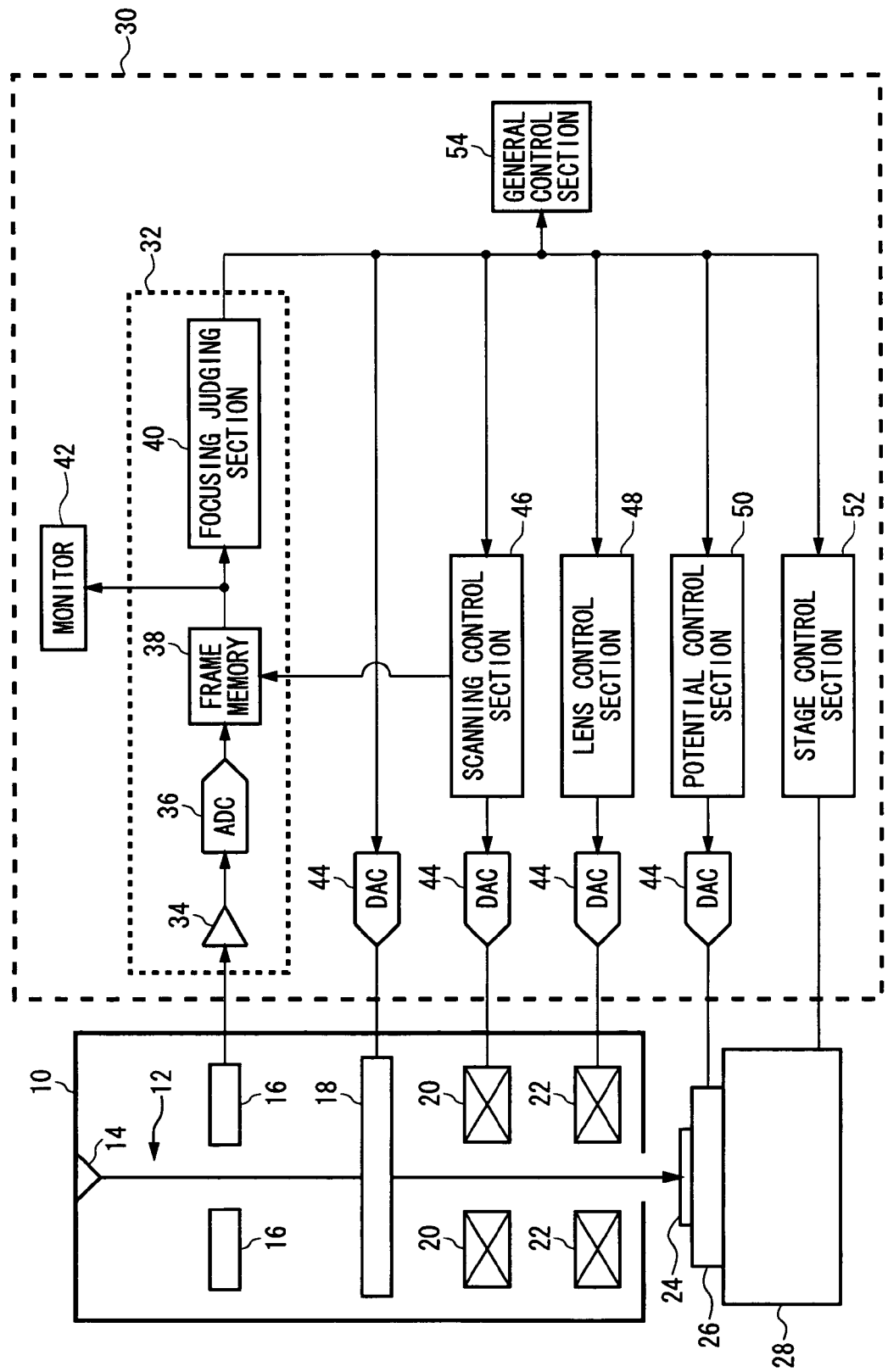
FIG. 1 is a diagram showing one exemplary configuration of a sample observing apparatus according to an embodiment of the invention.

FIG. 1 is a diagram showing one exemplary configuration of a sample observing apparatus 100 according to the embodiment of the invention. The sample observing apparatus 100 acquires an appearance of surface of a sample 24 to be observed by irradiating an electron beam 12 to the sample 24.

Operations of the sample observing apparatus 100 will be briefly explained at first. The sample observing apparatus 100 applies voltage to a sample holder 26 in correspondence to an amount of electric charge on the surface of the sample 24. Thereby, the sample observing apparatus 100 adjusts electric potential of the surface of the sample 24 to potential set in advance and irradiates the electron beam 12 to the surface of the sample 24 to acquire the appearance of surface of the sample 24. The amount of electric charge of the surface of the sample 24 may be measured beforehand to be given to the sample observing apparatus 100 or may be measured by the sample observing apparatus 100. The sample observing apparatus 100 measures the amount of electric charge of the surface of the sample 24 in the present embodiment.

Next, structural components of the sample observing apparatus 100 will be explained. The sample observing apparatus 100 is provided with a case 10, an electron gun 14, an electron detecting section 16, an energy filter 18, a deflector 20, a lens 22, a sample holder 26, a stage 28 and a control system 30. The electron gun 14, the electron detecting section 16, the energy filter 18, the deflector 20 and the lens 22 are stored in the case 10.

The electron gun 14 produces the electron beam 12. Negative acceleration voltage for accelerating the electron beam 12 in the direction of the sample 24 is applied to the electron gun 14. The deflector 20 deflects the electron beam 12 to a desirable spot on the surface of the sample 24. The deflector 20 deflects the electron beam 12 by generating an electric field for example.

The lens 22 focuses the deflected electron beam 12 on the surface of the sample 24. The lens 22 may be what alters a focus spot of the electron beam corresponding to a given electric current for example.

The sample 24 is mounted on the sample holder 26. Electric potential higher than that of the electron gun 14 is given to the sample holder 26 so that the electron beam 12 is accelerated in the direction of the sample 24. The sample holder 26 is mounted on the stage 28. The control system 30 changes the spot on the sample 24 to which the electron beam 12 is irradiated by moving the stage 28.

The electron detecting section 16 detects electrons produced when the electron beam 12 is irradiated to the surface of the sample 24. The energy filter 18 sequentially sorts reflected electrons having energy higher than a predetermined value and secondary electrons having energy lower than that of the reflected electrons among the electrons produced when the electron beam 12 is irradiated to the surface of the sample 24 and supplies them to the electron detecting section 16. The reflected electrons are electrons of the electron beam 12 reflected by the surface and the inside of the sample 24 and the secondary electrons are electrons emitted from the surface of the sample 24 when the electron beam 12 is irradiated to the sample 24.

The control system 30 has an appearance acquiring section 32, a monitor 42, a plurality of digital-analog converters (DAC) 44, a scanning control section 46, a lens control section 48, a potential control section 50, a stage control section 52 and a general control section 54.

The appearance acquiring section 32 acquires the appearance of surface of the sample 24 per each spot based on the electrons detected by the electron detecting section 16. The appearance acquiring section 32 acquires an image showing the shape of surface of the sample 24 for example. The appearance acquiring section 32 has an amplifier 34, an analog-digital converter (ADC) 36, a frame memory 38 and a focusing judging section 40 in the present embodiment.

The amplifier 34 amplifies a signal corresponding to the electrons detected by the electron detecting section 16 and supplies it to the ADC 36. The ADC 36 converts the received signal into a digital signal and supplies it to the frame memory 38. At this time, the frame memory 38 receives information specifying the position of the electron beam 12 being irradiated to the sample 24 from the scanning control section 46 for controlling the deflector 20 and stores the digital signal as image data in an address corresponding to the position of the electron beam 12.

The monitor 42 sequentially reads the image data stored in the frame memory 38 and displays the image. The focusing judging section 40 judges levels of focus of the electron beam 12 that vary corresponding to the amount of electric charge on the surface of the sample 24 based on the reflected electrons detected by the electron detecting section 16. In the present embodiment, the focusing judging section 40 judges the levels of focus of the electron beam 12 by analyzing the image data stored in the frame memory 38.

The scanning control section 46 controls the deflector 20 so as to irradiate the electron beam 12 to a desirable spot on the sample 24. The scanning control section 46 supplies a control signal to the deflector 20 via the DAC 44. In synchronism with the control signal supplied to the deflector 20, the scanning control section 46 sends a time reference signal to the frame memory 38 to store the image data of each frame in the frame memory 38.

The lens control section 48 controls the lens 22 to adjust the focus position of the electron beam 12. The lens control section 48 supplies a current for controlling the lens 22 via the DAC 44.

The potential control section 50 applies desired voltage to the sample holder 26 via the DAC 44. The stage control section 52 drives the stage 28 to adjust the spot on the surface of the sample 24 to which the electron beam 12 is irradiated. The general control section 54 controls these control sections in general.

Figure 2:
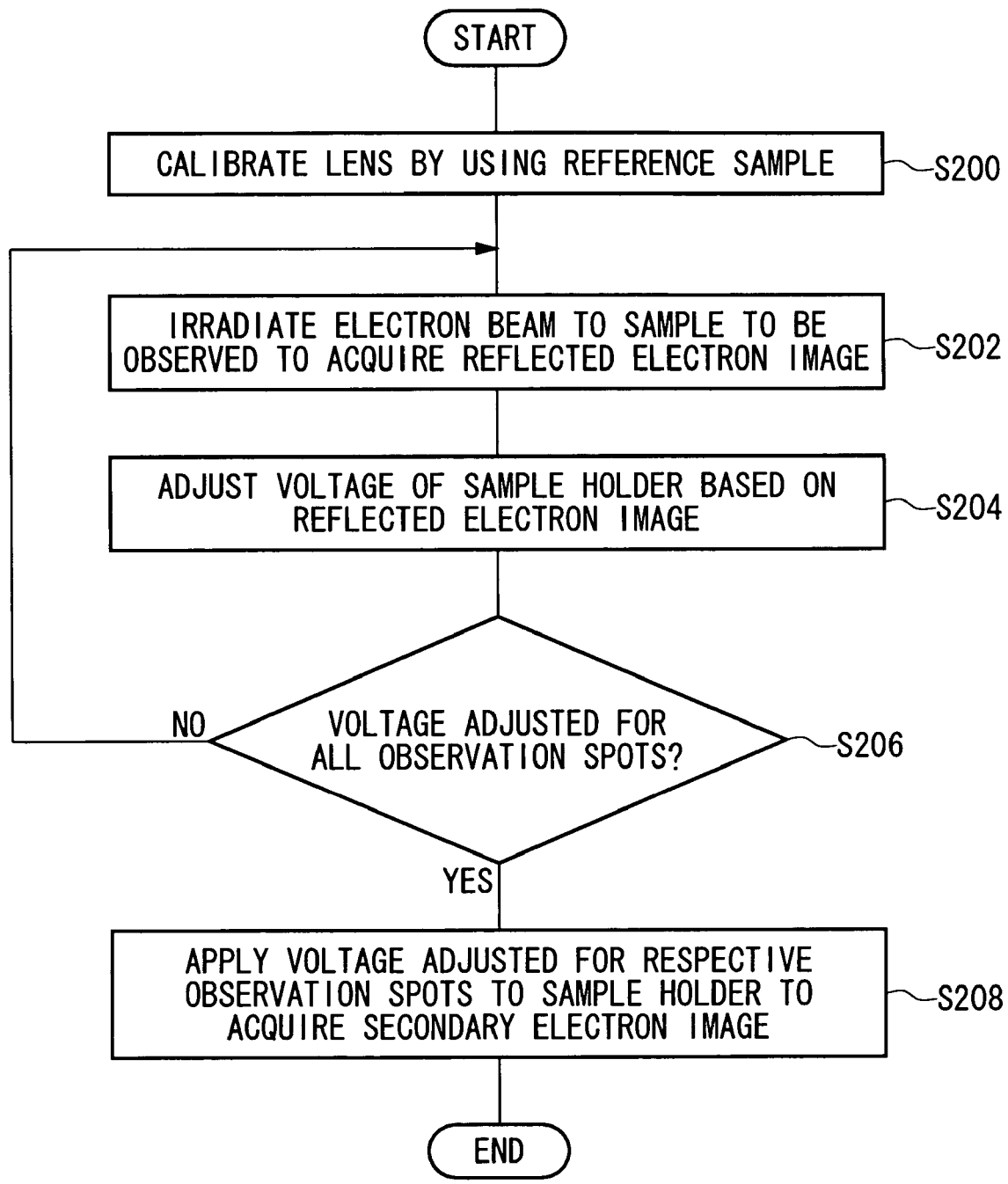
FIG. 2 is a flowchart explaining one example of operations of the sample observing apparatus.

FIG. 2 is a flowchart explaining one example of the operations of the sample observing apparatus 100. At first, calibration of the lens is carried out by using a reference sample in Step S200. The reference sample used here is a conductive material on which a pattern suitable for adjusting an optical system is formed and whose surface potential can be arbitrarily set. Height of the surface of the reference sample is almost equal to that of the surface of the sample 24 to be observed. The reference sample may be set on the sample holder 26 beforehand or may be a part of the sample 24.

In Step S200, the potential control section 50 applies reference voltage set in advance to the sample holder 26. Next, the electron gun 14 irradiates the electron beam 12 to the surface of the reference sample. At this time, the general control section 54 causes the energy filter 18 to sort the reflected electrons via the DAC 44 and causes the electron detecting section 16 to detect the reflected electrons. Then, based on the reflected electron image of the reflected electrons detected by the electron detecting section 16, the focusing judging section 40 judges the level of focus of the electron beam 12 on the surface of the reference sample. The general control section 54 informs the lens control section 48 of the result judged by the focusing judging section 40 and the lens control section 48 adjusts a control current supplied to the lens 22 so that the electron beam 12 is focused on the surface of the reference sample.

Next, the general control section 54 drives the stage 28 to irradiate the electron beam 12 to the desired spot on the surface of the sample 24 to be observed to acquire a reflected electron image in Step S202. In Step S202, the electron gun 14 irradiates the electron beam 12 to the surface of the sample 24 in the same manner with Step S200 and the electron detecting section 16 detects the reflected electrons. Then, the focusing judging section 40 judges the level of focus of the electron beam 12 on the surface of the sample 24 based on the reflected electron image. When the surface of the sample 24 has the reference potential at this time, the electron beam 12 is focused on the surface of the sample 24 and the appearance acquiring section 32 acquires the focused reflected electron image. When the surface of the sample 24 is charged with electricity and has potential different from the reference potential, the electron beam 12 is not precisely focused on the surface of the sample 24 and the appearance acquiring section 32 acquires an unfocused reflected electron image. Based on the acquired reflected electron image, the focusing judging section 40 judges the level of focus of the electron beam 12 that varies corresponding to the amount of electric charge on the surface of the sample 24.

Next, based on the acquired reflected electron image, the potential control section 50 adjusts voltage to be applied to the sample holder 26 in Step S204. Thereby, the potential control section 50 controls electric potential of the back of the sample 24 to adjust the potential of the surface of the sample 24 to the reference potential. For instance, the sample observing apparatus 100 acquires the reflected electron image while changing the voltage to be applied to the sample holder 26 and adjusts the voltage to be applied to the sample holder 26 so that the reflected electron image is focused. When the reflected electron image is unfocused for example, the focusing judging section 40 informs of that to the potential control section 50 via the general control section 54. The potential control section 50 changes the voltage to be applied to the sample holder 26 corresponding to the judged result of the focusing judging section 40 to focus the electron beam 12 on the surface of the sample 24. At this time, the potential control section 50 stores the adjusted voltage value and applies the stored voltage value in acquiring the secondary electron image in Step 208.

In Steps S202 and S204, the potential control section 50 adjusts the voltage to be applied to the sample holder 26 based on the reflected electron image per spot on the surface of the sample 24 to which the electron beam 12 is irradiated. In the present embodiment, the potential control section 50 has a memory for storing the spot on the surface of the sample 24 to which the electron beam 12 is irradiated correlatively with the adjusted voltage.

Next, it is judged whether or not the voltage to be applied to the sample holder 26 has been adjusted for all spots to be observed on the surface of the sample 24 in Step S206 and when there is an observation spot for which the voltage is not adjusted yet, the stage control section 52 drives the stage 28 so that the electron beam 12 is irradiated to that observation spot and repeats the operations of Steps 202 through 204. When the voltage to be applied to the sample holder 26 has been adjusted for all the observation spots, the stage control section 52 drives the stage 28 sequentially so that the electron beam 12 is irradiated to the respective observation spots and the potential control section 50 applies the voltage of the value adjusted for the respective observation spots sequentially to the sample holder 26 to acquire the secondary electron image in Step S208.

The control system 30 causes the electron beam 12 to be irradiated to the desired spot on the surface of the sample 24 in the same manner with Step S202 also in Step S208. At this time, the potential control section 50 applies the voltage corresponding to the spot on the surface of the sample 24 to which the electron beam 12 is sequentially irradiated to the sample holder 26 sequentially. The energy filter 18 supplies the secondary electrons to the electron detecting section 16 in the state in which the voltage adjusted by the potential control section 50 is applied to the sample holder 26 and the electron beam 12 is focused on the surface of the sample 24. Based on the secondary electrons detected by the electron detecting section 16, the appearance acquiring section 32 acquires a secondary electron image showing the appearance of surface of the sample 24 and displays it on the monitor 42.

The sample observing apparatus 100 described above is capable of adjusting the electric potential of the surface of the sample 24 to the reference potential set in advance by applying the voltage corresponding to the amount of electric charge of the surface of the sample 24 to the sample holder 26 to apply the voltage to the sample 24. Thereby, the electron beam 12 is precisely focused on the surface of the sample 24, allowing the appearance of surface of the sample 24 to be observed with precision. Still more, adjusting the electric potential of the surface of the sample 24 to the reference potential prevents the secondary electrons from being attracted to the electric charge of the sample 24 and allows the electron detecting section 16 to detect the secondary electrons with precision. Accordingly, the appearance acquiring section 32 can acquire the appearance of surface of the sample 24 with precision.

Still more, because the sample observing apparatus 100 is capable of applying the voltage corresponding to the amount of electric charge of each observation spot of the sample 24, it enables electric potential of all the observation spots of the sample 24 to be adjusted to the reference potential and the appearance of surface of the sample 24 to be observed. Therefore, even if the sample 24 has an area having a different amount of charge on the surface thereof, the sample observing apparatus 100 permits the appearance of surface of the sample 24 to be observed with precision.

Further, because the sample observing apparatus 100 judges the amount of electric charge on the surface of the sample 24 by using the reflected electrons, it is capable of judging the amount of charge on the surface of the sample 24 with precision. That is when the surface of the sample 24 is charged with positive electric charge, secondary electrons are attracted to the surface of the sample 24 and are barely detected by the electron detecting section 16. Accordingly, it is difficult to judge the level of focus by the secondary electron image. However, the electron detecting section 16 can detect the reflected electrons and the level of focus of the reflected electron image may be precisely judged even if the surface of the sample 24 is charged with the positive electric charge.

Still more, the appearance of surface of the sample 24 may be observed by using the secondary electron image whose spatial resolution is higher than that of the reflected electron image by switching the electrons detected by the electron detecting section 16 to the secondary electrons.

Figure 3:
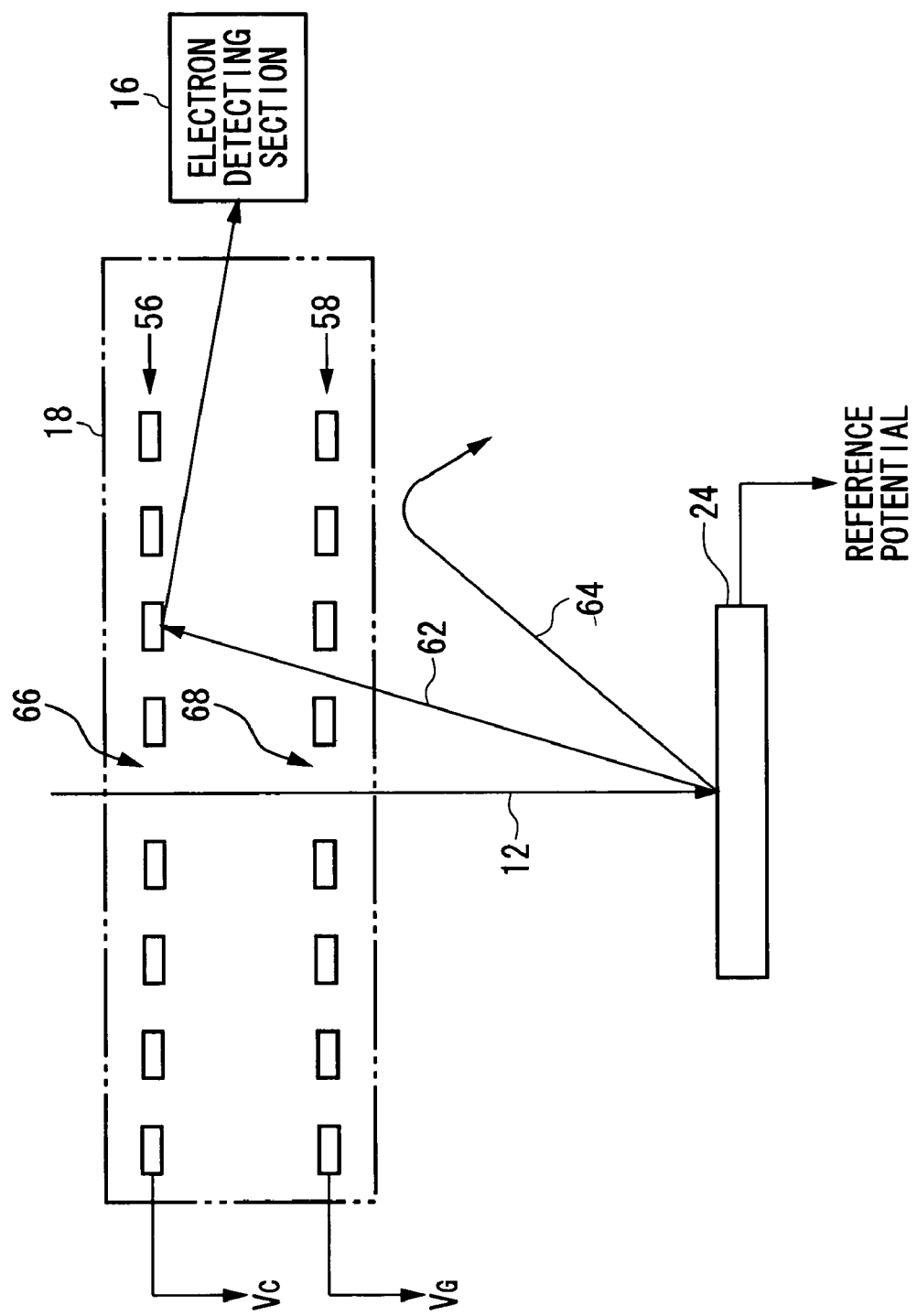
FIG. 3 is a diagram showing one exemplary configuration of an energy filter.

FIG. 3 shows one exemplary configuration of the energy filter 18. The energy filter 18 has a control electrode 56 and a grid electrode 58. The control electrode 56 is provided with through holes 66 for passing electrons in mesh and control voltage $V_C$ is applied thereto. The grid electrode 58 is provided between the control electrode 56 and the sample 24, is provided with through holes 68 for passing electrons in mesh and grid voltage $V_G$ is supplied thereto.

When the energy filter 18 sorts the reflected electron 62 to supply to the electron detecting section 16, negative grid voltage $V_G$ which is lower than the reference potential is applied to the grid electrode 58 and the control voltage $V_C$ whose voltage is higher than the grid voltage $V_G$ is supplied to the control electrode 56. When the grid voltage $V_G$ is $-50$ V and the control voltage $V_C$ is $-30$ V for example, the secondary electron 64 having low energy of less than 50 eV among the electrons produced when the electron beam 12 is irradiated to the sample 24 looses its energy before reaching to the grid electrode 58 and is unable to transmit the grid electrode 58. Then, only the reflected electron 62 having high energy of 50 eV or more passes through the grid electrode 58. In the present embodiment, the grid voltage $V_G$ that causes only the reflected electron 62 to pass through the grid electrode 58 is applied to the grid electrode 58.

The high energy reflected electron 62 that has passed through the grid electrode 58 collides against the control electrode 56. Thereby, the control electrode 56 emits electrons and the electron detecting section 16 detects those electrons. Preferably, the electron detecting section 16 has means for generating an electric field for inducing the electrons that have passed the grid electrode 58.

When the energy filter 18 sorts and supplies the secondary electron 64 to the electron detecting section 16, the positive grid voltage $V_G$ which is higher than that of the reference potential is applied to the grid electrode 58 and the control voltage $V_C$ which is higher than the grid voltage $V_G$ is applied to the control electrode 56. For instance, $+30$ V is applied as the grid voltage $V_G$ to the grid electrode 58 and $+50$ V is applied as the control voltage $V_C$ to the control electrode 56.

In this case, the reflected electron 62 and the secondary electron 64 pass through the grid electrode 58 and the electron detecting section 16 detects the reflected electron 62 and the secondary electron 64. However, because an amount of the reflected electrons 62 is very small as compared to an amount of the secondary electrons 64, an amount of electrons detected by the electron detecting section 16 is substantially equal to the amount of the secondary electrons 64. Through such configuration and control, the energy filter 18 sorts the reflected electron 62 and the secondary electron 64 and causes the electron detecting section 16 to detect them.

Figure 4A:
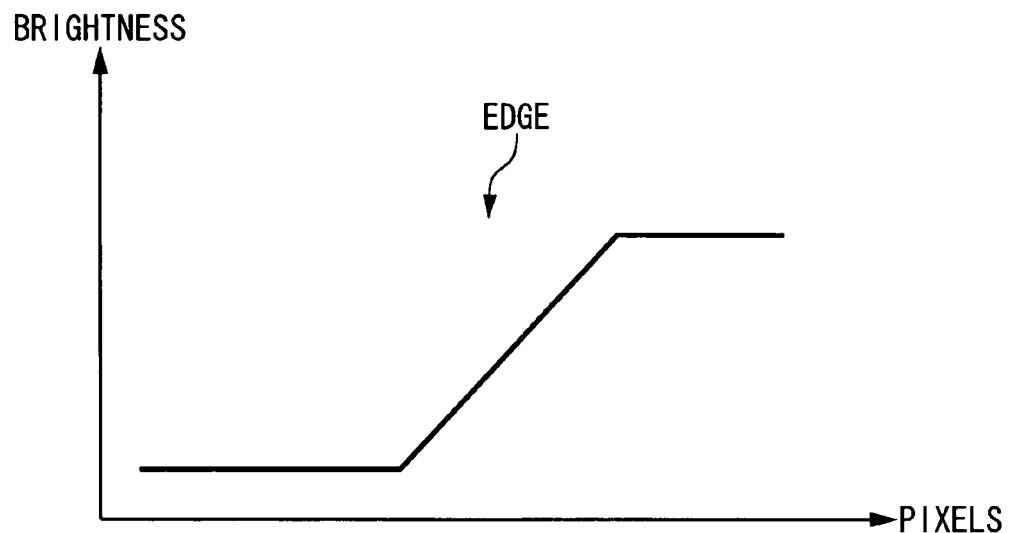
Figure 4B:
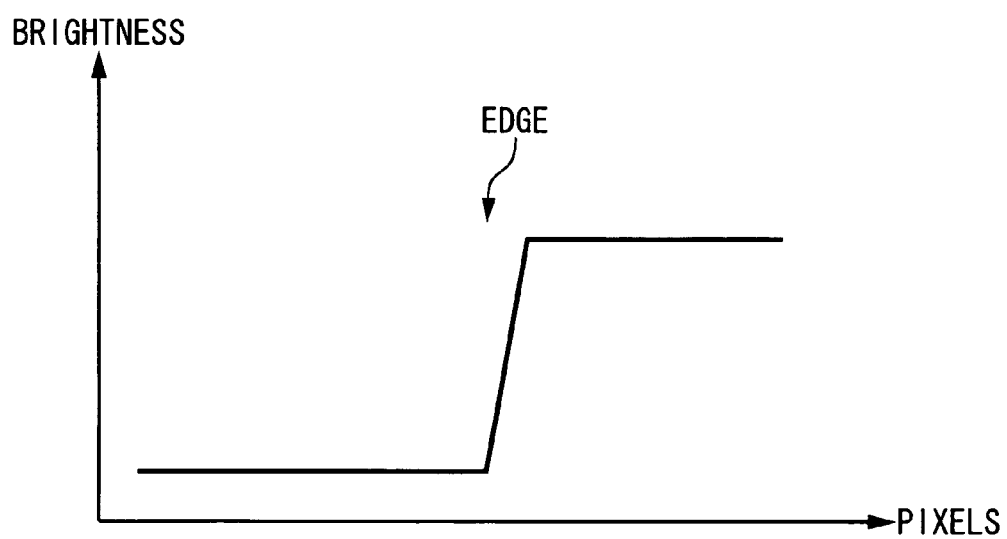

FIGS. 4A and 4B are graphs for explaining one example of a method for judging levels of focus in the focusing judging section. FIG. 4A shows brightness of pixels of a reflected electron image acquired by the appearance acquiring section 32 when the electron beam 12 is out of focus on the surface of the sample 24 and FIG. 4B shows brightness of pixels of a reflected electron image acquired by the appearance acquiring section 32 when the electron beam 12 is in focus. The horizontal axis represents respective pixels arrayed in the horizontal or vertical direction and the vertical axis represents brightness of each pixel.

When the electron beam 12 is in focus, brightness in an area of edge of a reflected electron image sharply changes as shown in FIG. 4B. When the electron beam 12 is out of focus, the reflected electron image is seen in blur, so that the change of brightness in the area of edge of the reflected electron image is moderate as shown in FIG. 4A as compared to the case when the electron beam 12 is in focus.

That is, the focusing judging section 40 may judge the levels of focus of the electron beam 12 based on the changes of brightness between pixels of the reflected electron image acquired by the appearance acquiring section 32 based on the reflected electrons. For example, it judges the level of focus of the electron beam 12 by calculating a differential value of brightness of the reflected electron image. Such a method allows the level of focus of the electron beam 12 to be readily judged.

As it is apparent from the above description, the invention allows the electron beam to be focused precisely on the surface of the sample to be observed and prevents the secondary electrons from being attracted to the electric charge of the sample 24. Thus, the invention enables one to observe the appearance of surface of the sample with precision.

Although the invention has been described by way of an exemplary embodiments, it should be understood that those skilled in the art might make many changes and substitutions without departing from the spirit and the scope of the invention. It is obvious from the definition of the appended claims that the embodiments with such modifications also belong to the scope of the invention.

What is claimed is:

1. A sample observing apparatus for observing the surface of a sample by irradiating an electron beam, comprising:
   an electron gun for irradiating the electron beam to the surface of said sample;
   a potential control section for adjusting electric potential of the surface of said sample to potential set in advance by applying voltage based on an amount of electric charge on the surface of said sample to said sample;
   an electron detecting section for detecting electrons produced when the electron beam is irradiated to the surface of said sample;
   an appearance acquiring section for acquiring the appearance of surface of said sample per each spot on the surface based on the electrons detected by said electron detecting section; and
   an energy filter for selectively sorting reflected electrons and secondary electrons from electrons produced when said electron beam is irradiated to the surface of said sample and supplying them to said electron detecting section, wherein the reflected electrons have energy higher than a predetermined value and secondary electrons have energy less than that of said reflected electrons.

2. The sample observing apparatus as claimed in claim 1, further comprising a sample holder for mounting said sample, wherein
   said potential controlling section applies the voltage corresponding to the amount of electric charge of the surface of said sample to said sample by applying it to said sample holder to adjust the electric potential of the surface of said sample to the potential set in advance.

3. The sample observing apparatus as claimed in claim 2, further comprising:
   a stage for mounting said sample holder; and
   a stage control section for driving said stage to control the spot on the surface of said sample to which said electron beam is irradiated,
   wherein said potential control section controls the voltage applied to said sample holder per each spot on the surface of said sample to which said electron beam is irradiated corresponding to the amount of electric charge per each spot on the surface of said sample to adjust the potential at each spot on the surface of said sample to the potential set in advance.

4. The sample observing apparatus as claimed in claim 3, wherein said potential control section has a memory for storing the spot on the surface of said sample correlatively with the voltage applied to said sample holder.

5. The sample observing apparatus as claimed in claim 1, further comprising:
   a focusing judging section for judging levels of focus of said electron beam that vary corresponding to the amount of electric charge on the surface of said sample based on the reflected electrons detected by said electron detecting section,
   wherein said potential controlling section adjusts the voltage to be applied to said sample holder based on the judged result of said focusing judging section to focus said electric beam on the surface of said sample.

6. The sample observing apparatus as claimed in claim 5, wherein
   said energy filter supplies the secondary electrons to said electron detecting section in a state when said electron beam is focused on the surface of said sample by said potential control section, and
   said appearance acquiring section acquires the appearance of surface of said sample based on the secondary electrons detected by said electron detecting section.

7. The sample observing apparatus as claimed in claim 5, wherein said focusing judging section judges the levels of focus based on the appearance of surface of said sample acquired by said appearance acquiring section based on the reflected electrons.

8. The sample observing apparatus as claimed in claim 7, wherein
   said appearance acquiring section acquires an image of the surface of said sample based on the electrons detected by said electron detecting section, and
   said focusing judging section judges the level of focus based on the variation of the brightness among pixels of the image acquired by said appearance acquiring section based on the reflected electrons.

9. A sample observing method for observing the surface of a sample by irradiating an electron beam, comprising:
   irradiating the electron beam to the surface of said sample;
   adjusting electric potential of the surface of said sample to potential set in advance by applying voltage determined based on an amount of electric charge on the surface of said sample to said sample;
   selectively sorting reflected electrons and secondary electrons from electrons produced when said electron beam is irradiated to the surface of said sample and supplying them to said electron detecting section, wherein the reflected electrons have energy higher than a predetermined value and secondary electrons have energy less than that of said reflected electrons;
   detecting electrons produced when the electron beam is irradiated to the surface of said sample; and
   acquiring an appearance of surface of said sample based on the electrons detected.

* * * * *